United States Patent
Gilbert et al.

(10) Patent No.: US 7,153,699 B2
(45) Date of Patent: Dec. 26, 2006

(54) MICROFABRICATED TWO-PIN SYSTEM FOR BIOMOLECULE CRYSTALLIZATION

(75) Inventors: John Gilbert, Brookline, MA (US); Jaishree Trikha, Waban, MA (US)

(73) Assignee: Cytonome, Inc., Watertown, MA (US)

( * ) Notice: Subject to any disclaimer, the term of this patent is extended or adjusted under 35 U.S.C. 154(b) by 477 days.

(21) Appl. No.: 10/328,932

(22) Filed: Dec. 23, 2002

(65) Prior Publication Data

US 2003/0170146 A1 Sep. 11, 2003

Related U.S. Application Data

(63) Continuation-in-part of application No. 10/027,171, filed on Dec. 21, 2001, now Pat. No. 7,041,257.

(60) Provisional application No. 60/427,423, filed on Nov. 19, 2002, provisional application No. 60/372,562, filed on Apr. 11, 2002.

(51) Int. Cl.
G01N 1/10 (2006.01)
G01N 1/00 (2006.01)
G01N 1/40 (2006.01)
B01L 3/02 (2006.01)

(52) U.S. Cl. ............ 436/180; 436/174; 422/100; 73/864.72

(58) Field of Classification Search ............ 436/174, 436/180; 422/100; 73/864.72
See application file for complete search history.

(56) References Cited

U.S. PATENT DOCUMENTS

| | | | |
|---|---|---|---|
| 3,885,440 A | 5/1975 | Rossfelder | |
| 3,984,307 A | 10/1976 | Kamentsky et al. | |
| 4,116,069 A | 9/1978 | Lezgintsev et al. | |
| 4,175,662 A | 11/1979 | Zold | |
| 4,659,677 A | 4/1987 | Glover et al. | |
| 4,756,427 A | 7/1988 | Gohde et al. | |
| 5,096,676 A | 3/1992 | McPherson et al. | |
| 5,256,241 A | 10/1993 | Noever | |
| 5,260,030 A | 11/1993 | DeVaughn | |
| 5,271,795 A | 12/1993 | Ataka et al. | |
| 5,552,127 A | 9/1996 | Asano | |
| 5,643,540 A | 7/1997 | Carter et al. | |
| 5,716,852 A | 2/1998 | Yager et al. | |
| 5,741,554 A | 4/1998 | Tisone | |
| 5,770,151 A | 6/1998 | Roach et al. | |
| 5,807,522 A | 9/1998 | Brown et al. | |
| 5,837,200 A | 11/1998 | Diessel et al. | |
| 5,932,100 A | 8/1999 | Yager et al. | |
| 5,957,167 A | 9/1999 | Feygin | |
| 5,961,934 A | 10/1999 | Arnowitz et al. | |

(Continued)

FOREIGN PATENT DOCUMENTS

DE 19843655 C2 3/2000

(Continued)

OTHER PUBLICATIONS

Blanchard, A.P. et al. "High-density oligonucleotide arrays" *Biosensors & Bioelectronics* 11(6/7):687-690 (1996).

(Continued)

*Primary Examiner*—Brian Gordon
(74) *Attorney, Agent, or Firm*—Lahive & Cockfield, LLP

(57) ABSTRACT

A two-pin liquid handling system for crystallizing biomolecules comprises a pair of interacting pins for holding a droplet of liquid therebetween. Each pin includes a tip spaced predetermined distance from the other pin to define a sample acquisition region. The two-pin liquid handling system includes a temperature and humidity control element for controlling the temperature of the sample acquisition region to cause transpiration of water to and from a droplet of biomolecule solution to promote crystallization of the biomolecule.

18 Claims, 9 Drawing Sheets

U.S. PATENT DOCUMENTS

| | | | |
|---|---|---|---|
| 5,962,329 A * | 10/1999 | Ershov et al. | 436/50 |
| 5,997,636 A | 12/1999 | Gamarnik et al. | |
| 6,001,231 A | 12/1999 | Kopf-Sill | |
| 6,024,925 A | 2/2000 | Little et al. | |
| 6,039,804 A | 3/2000 | Kim et al. | |
| 6,086,825 A | 7/2000 | Sundberg et al. | |
| 6,101,946 A | 8/2000 | Martinsky | |
| 6,110,426 A | 8/2000 | Shalon et al. | |
| 6,174,365 B1 | 1/2001 | Sanjoh | |
| 6,245,297 B1 | 6/2001 | Kowallis | |
| 6,255,119 B1 | 7/2001 | Baier | |
| 6,258,331 B1 | 7/2001 | Sanjoh | |
| 6,269,846 B1 | 8/2001 | Overbeck et al. | |
| 6,287,872 B1 * | 9/2001 | Schurenberg et al. | 436/181 |
| 6,296,673 B1 | 10/2001 | Santarsiero et al. | |
| 6,296,702 B1 | 10/2001 | Bryning et al. | |
| 6,303,387 B1 | 10/2001 | Birch et al. | |
| 6,309,891 B1 | 10/2001 | Shalon et al. | |
| 6,319,315 B1 | 11/2001 | Sanjoh | |
| 6,350,617 B1 * | 2/2002 | Hindsgaul et al. | 436/173 |
| 6,365,349 B1 | 4/2002 | Moynihan et al. | |
| 6,387,330 B1 | 5/2002 | Bova et al. | |
| 6,406,903 B1 | 6/2002 | Bray et al. | |
| 6,409,832 B1 | 6/2002 | Weigl et al. | |
| 6,413,586 B1 | 7/2002 | Vann et al. | |
| 6,417,007 B1 | 7/2002 | Gittleman et al. | |
| 6,461,572 B1 * | 10/2002 | Calfee et al. | 422/100 |
| 6,468,346 B1 | 10/2002 | Arnowitz et al. | |
| 6,637,473 B1 * | 10/2003 | Ganz et al. | 141/130 |
| 6,692,972 B1 * | 2/2004 | Yershov et al. | 436/180 |
| 6,875,402 B1 * | 4/2005 | Hirota et al. | 422/100 |
| 6,878,553 B1 * | 4/2005 | Li et al. | 436/174 |
| 2001/0005545 A1 | 6/2001 | Andou et al. | |
| 2001/0049149 A1 | 12/2001 | Kennedy et al. | |
| 2003/0148539 A1 * | 8/2003 | van Dam et al. | 436/180 |
| 2003/0166263 A1 * | 9/2003 | Haushalter et al. | 435/287.2 |
| 2004/0014042 A1 * | 1/2004 | Ju | 435/6 |
| 2004/0142460 A1 * | 7/2004 | Cima et al. | 435/287.9 |
| 2005/0019950 A1 * | 1/2005 | Gierde et al. | 436/177 |
| 2005/0079621 A1 * | 4/2005 | Elmes et al. | 436/43 |
| 2005/0112774 A1 * | 5/2005 | Gilbert et al. | 436/174 |
| 2005/0164326 A1 * | 7/2005 | Figeys et al. | 435/23 |

FOREIGN PATENT DOCUMENTS

| | | |
|---|---|---|
| WO | WO-03/000422 A1 | 1/2003 |

OTHER PUBLICATIONS

Lemieux, B. et al. "Overview of DNA chip technology" *Molecular Breeding* 4:277-289 (1998).

Schena, M. et al. "Microarrays: biotechnology's discovery platform for functional genomics" *Trends in Biotechnology* 16(7):301-306 (Jul. 1998).

Shalon, D. et al. "A DNA Microarray System for Analyzing Complex DNA Samples Using Two-color Fluorescent Probe Hybridization" *Genome Research* 6(7):639-645 (Jul. 1996).

Sieker. Microdialysis Crystallization Chamber: Design of a solvent exchangeable microdialysis crystallization system for manual or automatic control of protein crystal growth at microgravity. Journal of Crystal Growth. 1988. 90:349-357.

Weber. Physical principles of protein crystallization. Adv Protein Chem. 1991;41:1-36.

European Search Report Application No. 03721599.3-2113-US0310929, dated Apr. 15, 2005.

* cited by examiner

MICROFABRICATED TWO-PIN SYSTEM FOR BIOMOLECULE CRYSTALLIZATION

RELATED APPLICATIONS

The present application claims priority to U.S. provisional patent application Ser. No. 60/427,423, filed Nov. 19, 2002, and U.S. provisional patent application Ser. No. 60/372,562, and is a continuation-in-part of U.S. Pat. application Ser. No. 10/027,171, filed Dec. 21, 2001 now U.S. Pat. No. 7,041, 257. The present application is further related to patent application 10/328,931, entitled "Microfluidic Chip for Biomolecule Crystallization," filed on even date herewith. The contents of each of the foregoing patent applications are expressly incorporated herein by reference.

FIELD OF THE INVENTION

The present invention relates to a liquid handling system for handling a liquid sample. More particularly, the present invention relates to a liquid handling system for crystallization of macromolecules, such as proteins.

BACKGROUND OF THE INVENTION

The understanding of specific properties, functions and three-dimensional structure of proteins is an invaluable asset for understanding protein-ligand interaction and rational drug design. From the basic biochemical standpoint, for example, information on the three-dimensional structure of protein or the like is the basis to understand the functional role of molecules in a biochemical system.

In analyzing the structure of proteins, it is generally desirable to grow X-ray diffraction quality crystals from small quantities of a biomolecule. However, structural analysis of protein is currently a labor-intensive, lengthy process that requires significant consumption of expensive macromolecules and reagents. With the advent of robust expression and protein purification systems, high intensity, synchrotron x-ray sources and computer based methods of solving diffraction patterns, a rate limiting step in structural studies lies in rapidly growing x-ray quality crystals from small quantities of biomolecule.

SUMMARY OF THE INVENTION

The present invention provides for methods and hardware for growing crystals of biological macromolecules using real-time, or dynamic, control of parameters that promote crystal growth from protein solution. Many prior crystallization devices available for high throughput screening of crystallization conditions are incapable of addressing crystallographers' requirements for an efficient crystallization system. The present invention provides a fluid sample handling system comprising two microfabricated interacting pins for forming and handling droplets of a biomolecule solution and forming crystals of the biomolecule. The pins are spaced a predetermined distance from each other at their tips to define a sample acquisition region. The pins acquire and hold a droplet of the biomolecule solution in the sample acquisition region formed in the space between the tips and concentrate the biomolecule solution to promote crystal growth.

The present invention provides a system and methods for growing crystals of biological macromolecules using real-time, or dynamic, control of parameters that promote crystal growth from the protein solution. The crystallization system of the present invention is capable of forming a high resolution quality crystal using between about one and about ten nanograms of a biomolecule, such as protein. The present invention provides an automated system that may test up to 1000 conditions per day using only 5–50 micrograms of the target biomolecule. Each test can be monitored in real-time for successful crystal formation, resulting in fine adaptive control of the automation system. Each successfully formed crystal may be frozen in place, which is also appropriate for taking the crystal directly to diffraction studies.

DETAILED DESCRIPTION OF THE ILLUSTRATIVE EMBODIMENTS

Figure 1A:
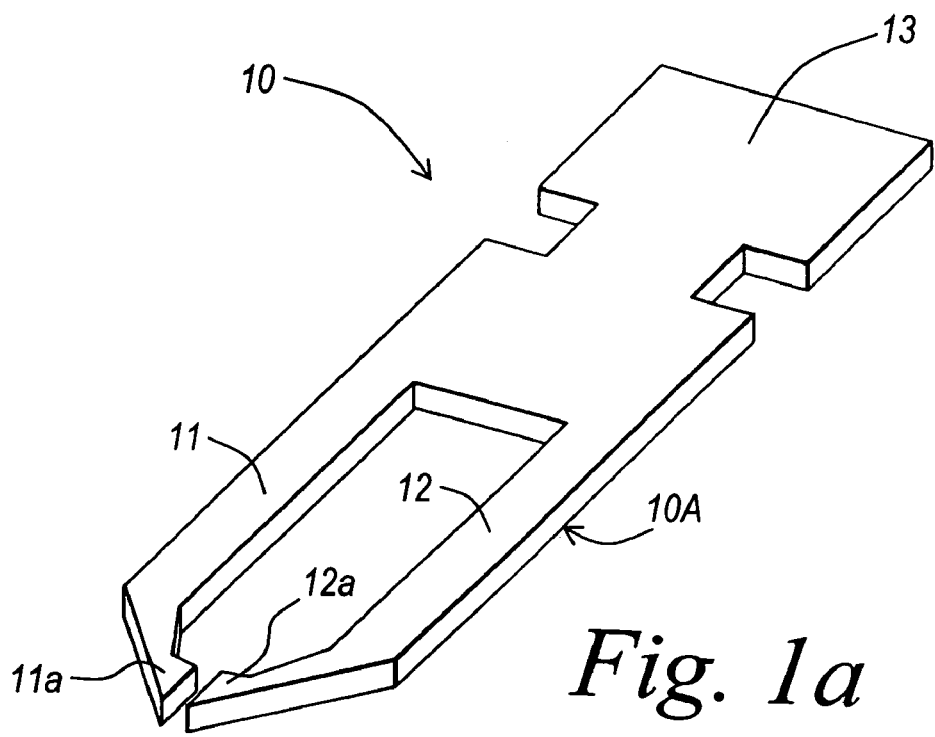
FIG. 1a illustrates a microfabricated fluid handling system employing a pin assembly according to the teachings of the present invention.

The present invention provides a fluid handling system for handling a predetermined volume of a fluid, such as a liquid sample. The system of the present invention provides for precision handling of a liquid sample by a fluid handling system using two interacting pins. The fluid handling system is suitable for use in a basic research or a commercial environment to promote biomolecule crystallization. The invention will be described below relative to an illustrative embodiment. Those skilled in the art will appreciate that the present invention may be implemented in a number of different applications and embodiments and is not specifically limited in its application to the particular embodiment depicted herein.

As used herein, the term "handling" is intended to include manipulating, retrieving, dispensing, acquiring or delivering a fluid, or any other suitable means for conveying the fluid.

As used herein, the term fluid is intended to include any type of liquid or gas, including, for example, a biological, biochemical or chemical sample, analyte, reagent, precursor for synthesis, or buffer. The fluidcan ne employed during use with a microfluidic system.

As used herein, the terms "protein solution" or "biomolecule solution" includes a solution comprising a molecule to be crystallized, e.g. protein or biomolecule.

The term "protein" is exemplary and it is understood that the present invention can be used to crystallize materials susceptible or capable of being crystallized under the conditions described herein. For example, molecules that can be used with the present invention include proteins, nucleic acids, e.g., DNA or RNA, co-factors, substrates, substrate analogs, or derivatives of any of these molecules. Further, the present invention is intended to be used with fragments of biomolecules, e.g. peptides or nucleic acid fragments. The present invention is also intended to be used with modified, e.g., in vivo or in vitro, macromolecules. For example, protein molecules can be modified in vivo, e.g., glycosylated, myristolated, or adenylated. Alternatively, protein molecules may be modified in vitro, e.g., chemically modified. The present invention is also intended to be used in co-crystallization or crystallization of complexes of any of the biomolecule types above.

The terms "effector" or "effectors" represent all the possible solutes or components or conditions of a buffer that might be set as the conditions to promote crystallization. The terms include, but are not limited to, ions, pH, temperature, detergents, and other molecules and components known to those skilled in the art of biomolecule crystallization.

The term "transpiration" as used herein refers to the exchange of fluid between a sample and the environment, including the process of evaporation.

The term "integration ratio" means the ratio of protein incorporated into the crystal as compared to the total amount of protein consumed in attempting to grow a crystal. In a major improvement over other crystallization techniques, the present method allows crystal growth from small amounts of purified macromolecule. The crystals resulting from this new method are comparable in size to crystals grown by other techniques, despite using approximately two orders of magnitude less starting material. In one embodiment the integration ratio of polypeptide in the crystal as compared to total protein used to grow the crystal is 1:50, 1:100, 1:150, 1:200, 1:250, 1:300, 1:400, 1:500, 1:750,1: 1000, 1:1500, 1:2000, 1:2500, 1:3000, 1:4000, 1:5000, 1:6000, 1:7500, 1:10,000, 1:20,000, 1:30,000, 1:40,000, 1:50,000. It should be understood that any of the above ratios can be the beginning or end point for a range of ratios over which the instant invention is intended cover.

The term "static crystallization condition" is defined wherein the various parameters that effect crystallization are varied by mixing macromolecules with different effectors including buffers, precipitating agents, additives, ligands and, substrates.

In conventional crystallization experiments static conditions are set and the solution conditions are then allowed to "drift." The term "drift" means allowing the various effectors in crystallization conditions to change in an uncontrolled manner until crystallization takes place or such a length of time passes that one gives up on that set of static conditions. For example, in a currently available hanging drop method concentration of protein in the drop is allowed to equilibrate with the reservoir solution so that the concentration of the protein in the drop increases at an uncontrolled rate till the crystals appear in the drop. In conventional systems "static conditions" followed by "drift" as described above are employed to test for each successful crystallization condition.

The term "dynamic open-loop condition" is defined wherein an effector is set to vary at a controlled rate and the rate is pre-set. For example one might set the pH to be varied by 0.05 pH units per second or set the protein concentration to increase by 0.5 mg/ml per second.

To apply dynamic open-loop conditions, one must be able to control effector levels with a useful precision that is preferably better than 30% of the full scale variation and most preferably better than 10% of the full scale variation and do so over a useful rate that is preferably over minutes and most preferably over seconds.

The term "dynamic closed-loop condition" is defined by an effector being set to be varied from an initial setting in response to a program that takes into account real time observations of the crystallization process. In one example the protein concentration is set to increase at 0.5 mg/ml per second until a crystal is observed to start forming and after that time the protein concentration is held fixed. In another example the NaCl concentration is set to increase at a rate of 100 mM/sec until a crystal is observed to initiate and then the NaCl concentration is reduced by 10 mM/sec until the crystallization process is completed. By changing an effector in response to the development of the first crystal one may avoid the formation of multiple crystals.

To apply dynamic closed-loop conditions, one must be able to control effector levels with a useful precision that is preferably better than 30% of the full scale variation and most preferably better than 10% of the full scale variation and do so over a useful rate that is preferably over minutes and most preferably over seconds. One must also be able to observe the process of crystallization or the state of the crystallization solution in real time in order to make controlled changes in the target effector levels in response to those observations.

The ability to use either open or closed loop dynamic conditions for crystallization is particularly significant because the quality and number of crystals formed is strongly sensitive to the dynamics of the crystal formation process.

In the most general type of conditions for crystallization wherein some set of effectors are to be set, some of those effectors may be static conditions, some may be open-loop dynamic conditions and some may be closed-loop dynamic conditions. The rates of change set for the effectors subject to open-loop dynamic conditions may be the same or they may be different. The rates of change and the response program for effectors subject to closed-loop dynamic conditions may be the same or they may be different. Certain methods of effector change such as evaporation are only suited for changing all molecular concentrations in the test solution simultaneously and at the same rate. Microdialysis and microfiltration can be used to change the concentrations of different molecules at different rates.

The "response time" of a system for changing effector levels is the minimum time required to change an effector and have it equilibrate through the solution. For this purpose working with smaller volumes reduces response time of any system. In particular the current invention associated with dynamically changing effector levels in nanoliter scale volumes is preferred over those using larger volumes.

The term crystallization "condition space for a set of effectors" means all the possible ways to set those effectors in experiments to test for crystallization. This includes using static, open-loop dynamic and closed-loop dynamic settings. The condition space for a set of effectors that includes the open-loop dynamic and closed-loop dynamic options is larger than the condition space for that set of effectors without those options.

The present invention discloses a fluid handling system for producing crystals of new biomolecules or new crystal forms of previously crystallized biomolecules.

The term "useful in structural determination" refers to crystals that can be harvested from the crystallization trial and subjected to x-ray crystallography. The methods of the present invention allow for testing of many sets of crystallization conditions and, unlike the methods currently available in the art, allow for removal of crystals from the microfluidic chip to be used in x-ray crystallographic structural determination.

Figure 1B:
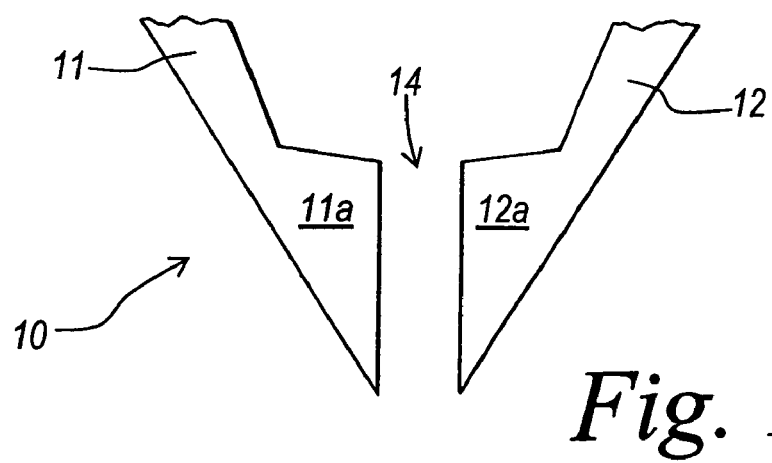
FIG. 1b illustrates a tip region of the fluid handling system of FIG. 1a, which according to one embodiment is fabricated to hold about 1.2 nanoliters of liquid.

FIGS. 1a and 1b illustrate a microfabricated fluid handling system 10 according to the teachings of the present invention. The fluid handling system 10 includes a pin assembly, generically designated as assembly 10A, that includes at least a pair of pins sized and configured to hold a droplet of fluid between the tips of the pins. Specifically, the pin assembly comprises a first pin 11 and a second pin 12, which are connected to a holder 13. The pin tips 11a and 12a are separated by an initial separation distance D (FIG. 2a) to form a fluid or sample acquisition region 14 in the space between the tips. For purposes of simplicity, we will describe the fluid handling system of the invention as handling a liquid sample.

To acquire a droplet of a liquid sample, such as a protein solution containing a protein to be crystallized, the pin tips 11a, 12a are immersed in a reservoir containing a supply of a selected liquid sample. The pin tips 11a, 12a are positioned to allow capillary flow into a sample acquisition region 14. The capillary force induced in the sample acquisition region 14 pulls a droplet, having a volume defined by the separation distance and shape of the pin tips 11a, 11b, into the sample acquisition region 14. The capillary force produced between the surfaces of the pin tips holds the droplet in the sample acquisition region 14 formed between the two pin tips 11a, 11b. As shown in FIG. 1b, the fluid handling system may be used to hold a droplet having a volume of between about 0.1 nanoliters and about 50 nanoliters. FIG. 1b illustrates a fluid handling system holding a 1.2 nanoliter volume of liquid in the sample acquisition region between the tips 11a, 11b, though one skilled in the art will recognize that the invention is not limited to the described volume.

Figure 2A:
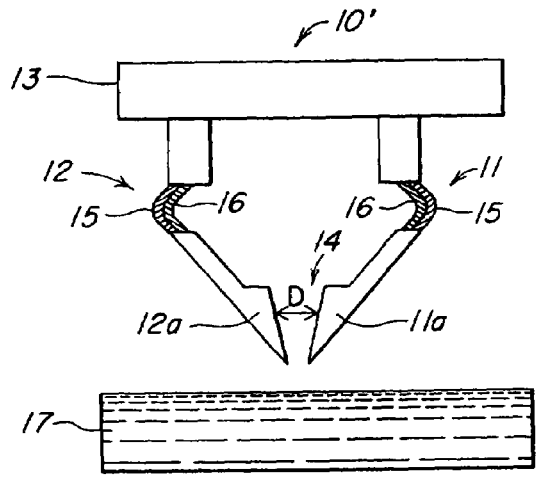
FIGS. 2a and 2b illustrate the operation of the fluid handling system in a sample acquisition mode according to the teachings of the present invention.
Figure 2B:
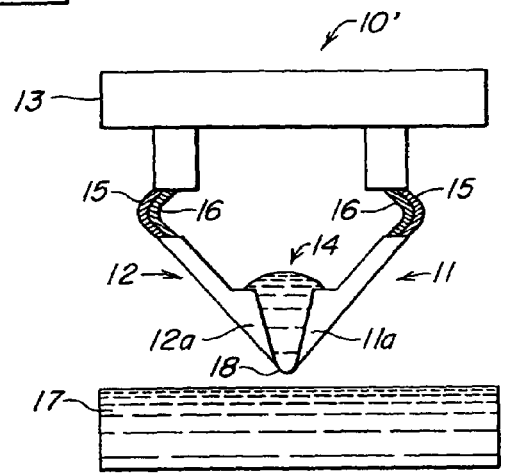

FIGS. 2a and 2b illustrate another embodiment of the fluid handling system according to the teachings of the present invention. The illustrated fluid handling system 10' is illustrated in a sample acquisition mode for acquiring a droplet of a liquid sample having a predetermined volume from a reservoir containing a supply of the liquid sample. Like parts are designated with the same reference numerals. The fluid handling system 10' of FIGS. 2a and 2b comprises a pair of separately movable interacting pins sized and configured to hold a droplet of liquid between the tips of the pins. Similar to the fluid handling system 10 of FIG. 1, the fluid handling system 10' comprises a first pin 11 and a second pin 12; which are separated by an initial separation distance D to form a sample acquisition region 14 in the space between the tips. The tips 11a and 12a may be movably coupled or connected to a holder 13. The position of each pin is controlled using actuators 15 located in one or more of the pins 11 and 12. According to an alternate embodiment, one or more sensors 16 can be optionally provided on one or more of the pins 11 and 12 to sense movement of the pin. The sensor can generate an output signal that can be received and used by associated circuitry or a controller for determining or measuring the separation distance D between the pin tips 11a, 12a. Those of ordinary skill in the art will readily recognize that the holder of the invention can include any suitable structure for supporting, retaining, affixing, securing or holding the pins. The illustrated holder 13 can include one or more support stanchions 13a for coupling to the pin assembly.

To acquire a droplet of a liquid sample, such as a protein solution containing a protein to be crystallized, the pin tips 11a, 12a are immersed in a reservoir 17 containing a supply of a selected liquid sample. The pin tips 11a, 12a are positioned to allow capillary flow into to sample acquisition region 14. The capillary force induced in the sample acquisition region 14 pulls a droplet 18, having a volume defined by the separation distance of the pin tips 11a, 11b, into the sample acquisition region 14. The capillary force produced between the surfaces of the pin tips holds the droplet in the sample acquisition region 14 formed between the two pin tips 11a, 11b. The actuators 15 in the pins 11, 12 move the pins to vary the separation distance D between the tips, thereby varying the amount of sample that is acquired by the two-pin fluid handling system, or to handle the sample therefrom.

According to one practice, the fluid handling system of the invention is configured to handle (e.g., acquire) liquid samples in volumes between about 0.1 nanoliters and about 50 nanoliters. One skilled in the art will recognize that the acquired volume is not limited to this range and that the pins may be spaced apart to accommodate any suitable volume of liquid.

The actuators 15 can also compensate for varying physical properties of the particular liquid sample, such as viscosity, surface tension, and the like, by modifying the separation distance D between the pins. The sensors 16 may also be utilized to measure the force applied between the tips and the physical properties of the acquired liquid sample on the fly. In this manner, the settings (i.e. the pin separation distance) of the pin fluid handling system 10' can be modified to compensate for variations in the measured properties of the liquid sample in real time.

According to the illustrative embodiment, the fluid handling systems 10, 10' and/or pin assemblies 10A are fabricated from a silicon wafer using a microfabrication technique, such as a standard photolithography etching process, to fabricate the pin structures. One skilled in the art will recognize that alternative materials and manufacturing techniques may be utilized. For example, the fluid handling system may be made out of glass, plastic or any other suitable material. According to one embodiment, an array of fluid handling systems 10, each comprising two pins forming a channel therebetween, may be formed on a single substrate, such as a silicon wafer. For example, an array of up to about 300 or more systems 10 may be formed on a four-inch silicon wafer.

Figure 3:
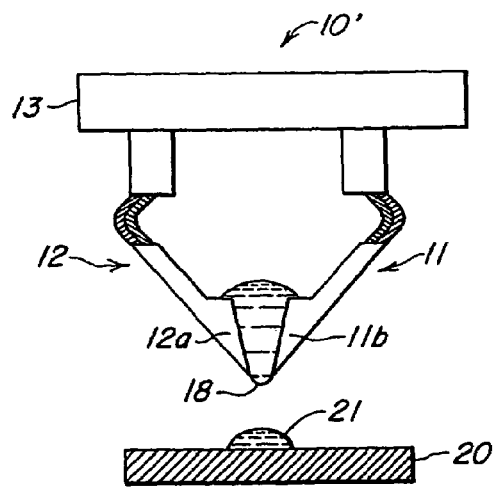
FIG. 3 illustrates the fluid handling system of FIGS. 2a and 2b in a spotting mode according to the teachings of the present invention.

FIG. 3 illustrates the fluid handling system 10' of the invention disposed in a sample spotting mode. The fluid handling system 10' may be utilized as a spotting system for printing or discharging arrays of biochemicals, such as nucleic acid molecules or proteins, or other suitable liquid samples to a sample handling system, such as a printing substrate, titre plate, microfluidic system or device, and the like for use in proteomics, genomics, screening, diagnostics and other applications. After the fluid handling system acquires a droplet, the fluid handling system is moved in close proximity to a surface 20. The surface 20 may comprise a solid surface or a liquid. The surface 20 may comprise a porous structure, such as a porous membrane, or a non-porous structure, such as a microscope slide. The loaded pins deposit a spot 21 on the surface 20 having a selected spot volume by direct contact between the pin tips 11a, 11b and the surface. The separation distance D2 during contact may be varied to increase or decrease the volume of the dispensed spot of the liquid sample. According to the illustrative embodiment, the volume of the dispensed spot 21 is significantly smaller than the volume of the acquired droplet 18, and is generally sub-nanoliter in volume, though one skilled in the art will recognize that the invention is not limited to this range.

The use of the two-pin fluid handling system of the illustrated embodiment in spotting applications provides enhanced control over the size of the deposited spots in a microarray, and also allows for smaller spots to be formed and deposited.

Figure 4A:
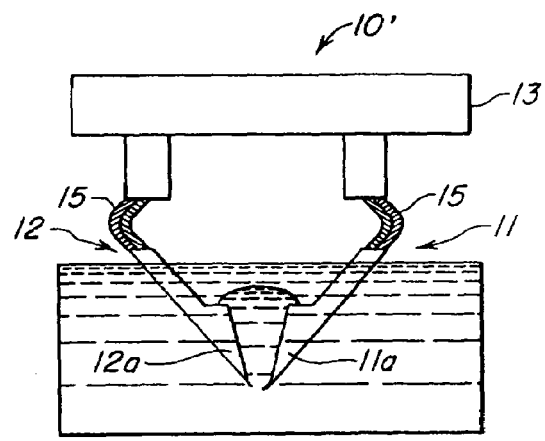
FIGS. 4a and 4b illustrate the fluid handling system of FIGS. 2a and 2b in a dilution mode according to the teachings of the present invention.
Figure 4B:
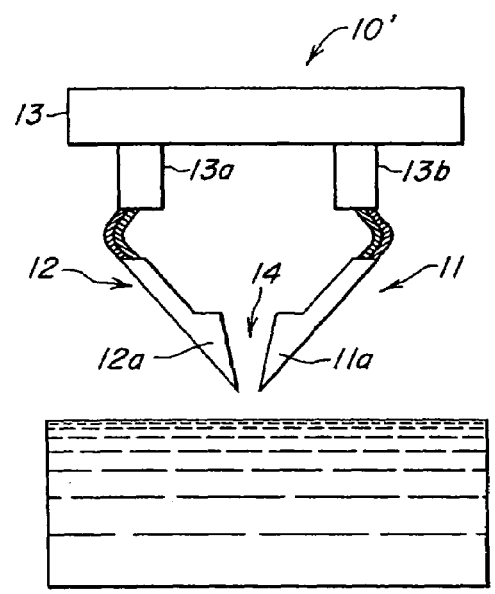

The fluid handling system may further be utilized as a wet deposit system with dilution to dilute a selected volume of a first liquid in a second liquid sample. FIGS. 4a and 4b illustrate the fluid handling system 10' in a dilution mode, wherein the acquired droplet 18 of a sample is diluted in a larger supply of a target fluid 30. After the fluid handling system 10' acquires a droplet 18, the size of which is defined by the separation distance of the pin tips 11a, 12a, the pin tips 11a, 12a are immersed in a reservoir 30 containing a target fluid. The droplet 18 automatically dilutes into the target fluid via mixing and diffusion. To accelerate the dilution process, the separation distance of the tips 11a, 12a may be increased during dilution using the actuators 15.

Figure 5:
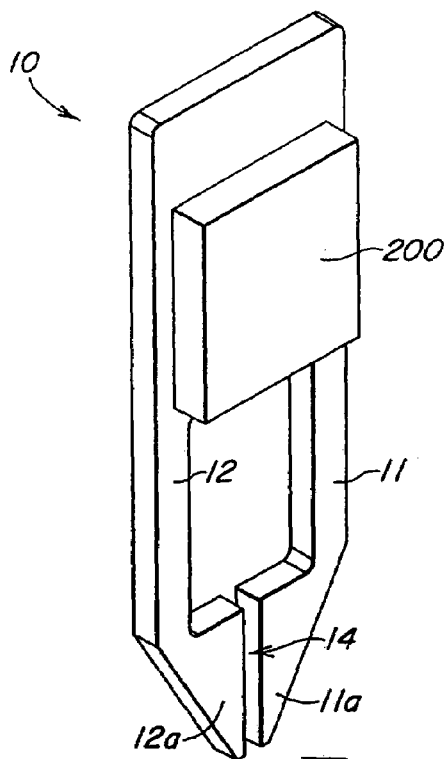
FIG. 5 illustrates another embodiment of the fluid handling system including a temperature control element according to the teachings of the present invention.

FIG. 5 illustrates another embodiment of the fluid handling system of the present invention. Like parts are designated with like reference numerals. The illustrated fluid handling system 10 includes a temperature control element 200 for controlling, varying or regulating the temperature of the liquid sample being handled. The temperature-controlled fluid handling system 10 comprises a first pin 11, a second pin 12 and a temperature control element 200 for controlling the temperature of the pin assembly and/or the liquid sample. For example, the temperature control element can heat or cool the pin assembly or the liquid sample. The temperature control element can be any device suitable for cooling or heating any component of the fluid handling system 10, and is preferably a thermoelectric module, such as a Peltier element. The temperature control element can form part of the fluid handling system 10, the pin assembly 10A, or can be provided as a separate independent component. The first pin 11 and the second pin 12 are positioned relative to each other to form a sample acquisition region, illustrated as a channel 14 formed between the two tip elements 11a and 12a defining the sample acquisition region. The temperature control element 200 is coupled, connected, affixed, secured or otherwise disposed in temperature communication with a surface on a base or sample-receiving substrate. Upon activation of the temperature control element 200, the temperature of the fluid handling system 10 is changed, to either promote or control evaporation of the sample.

One skilled in the art will recognize that any suitable means for controlling the temperature of the liquid carried by the pin of the fluid system may be utilized according to the teachings of the invention.

Figure 6:
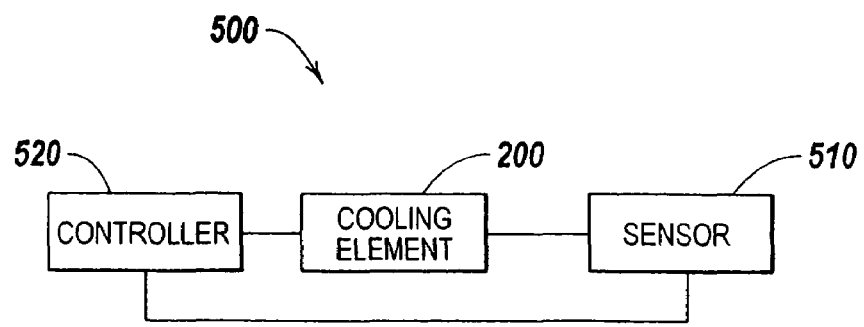
FIG. 6 is a schematic block diagram of a temperature control system suitable for operation with the fluid handling system of FIG. 5.

According to another embodiment of the invention, the temperature-controlled fluid handling system 10 may further include a temperature control circuit, shown in FIG. 6, for controlling the temperature of the system 10 or the liquid sample carried by the system. For example, the temperature-controlled fluid handling system 10 may include a temperature control system 500 for comparing an actual temperature of a component of the system, such as one of the pins or the liquid sample, to a reference temperature and adjusting the actual temperature to reduce any deviation between the actual temperature and the reference temperature. The temperature control system 500 includes a temperature sensor 510 for continuously measuring the temperature of the liquid sample or fluid system and a controller 520 for controlling the temperature control element 200 in response to the temperature detected by the sensor 510. The controller 520 compares the detected temperature to the set reference temperature. If the detected temperature deviates from the set reference temperature, the controller 520 triggers the cooling element 200 to increase or decrease cooling, in order to maintain the temperature of the system or liquid at the set reference temperature. Although illustrated as a feedback system, those of ordinary skill will readily recognize that the system 500 can also be configured as an open loop system.

The sensor 510 may comprise a thin film resistor, formed of conductive metals, carbon, a semi-conductor or any suitable material. The sensor is preferably integrated with the temperature-controlled fluid system and continuously measures the operating temperature of the system 10. One skilled in the art will recognize that any suitable temperature sensor and controller may be utilized in order to actively control the temperature of the fluid handling system.

As set forth, the device 10 of an illustrative embodiment of the invention comprises a picoliter—nanoliter silicon pipette suitable for acquiring and handling small volumes of liquid sample. According to one application, the temperature-controlled two-pin system 10 may be used as a crystallization device to form crystals from a protein or other biomolecule. The crystallization device can be programmed to automatically and very precisely pickup nanoliter amounts of a biomolecule sample to promote crystallization of a molecule in the biomolecule sample. As shown, in this application the pins 11, 12 form micro and picoscale crystallization cavities for crystallization purposes. By using these specially designed crystallization cavity devices, experiments can be done using nanogram quantities of protein or other biomolecule, a reduction in consumption of material by at least two orders of magnitude over conventional methods. By using automation designed around crystallization cavity devices, it is possible to simplify the crystallization process, create higher quality crystals and develop more reproducible processes for crystallization while reducing reagent consumption.

The crystallization process includes three stages: nucleation, crystal growth and cessation of crystal growth. During nucleation, an initial cluster of molecules associate in repeating units in three dimensions to form a thermodynamically stable aggregate. Crystals form in supersaturated solutions in which the protein concentration exceeds a nucleation concentration. Crystal growth ceases when the protein solution is sufficiently depleted of protein molecules or when other conditions change to modify the nucleation concentration. Proteins are generally induced to crystallize by adding agents that either alter their surface chargers or perturb the interactions between the protein and bulk solvent water to promote associations that lead to crystallization.

According to one embodiment, the two-pin system 10 may be used to grow protein crystals by mixing the protein to be crystallized with the crystallizing agents and adding the protein solution to a well. Initially, the protein concentration is less than the nucleation concentration. The crystallization conditions may be set in the well by exchanging dialyzable effectors, such as ions, water, small molecules, buffer, pH, ligands or other dialyzable effectors of crystallization, and/or altering the temperature of the protein solution. After setting the crystallization conditions by setting effectors in the well containing the protein solution, the two-pin device 10 may be used to pick up a nanoliter volume of the protein solution in the space between the tips 11a, 12a. Preferably, the volume of acquired protein solution is between about 0.1 and about 50 nanoliters. Next, the protein is concentrated by transpiration of water to or from the protein solution between the tips 11a, 12a to promote crystal formation. Transpiration may be controlled by controlling the temperature, humidity, the volume of the space 14 between the tips and/or shape of the region between the tips. As a result of the controlled transpiration, and resulting increase in the protein concentration, a crystal forms and is held between the pin tips 11a, 12a.

One skilled in the art will recognize that the crystallization device may also be used to crystallize other biomolecules or to co-crystallize combinations of biomolecules in a similar process to that described above.

The formation of the crystal may be observed in situ without requiring transfer of the formed crystal from the device 10. Because the tips 11a, 12a are open to the transmission of light and the sample acquisition region 14 is an open, rather than closed, cavity, the formation of the crystal may be observed using optical means. According to one embodiment, polarized light optics and CCD camera may be used to detect presence of crystals, though other suitable observation means may also be used. The ability to observe the formation process and the resulting crystal in situ allows for real time dynamic control of the crystallization conditions. Initialization of crystal formation may be observed and that observation may be used in real time to change or stabilize the protein crystallization conditions. For example, crystal formation may be observed and the temperature of the tips may be altered in real time using the temperature control element 200 to optimize crystal growth. Alternatively, the humidity may be altered in response to the observation. The crystal may be frozen and observed at intermediate points during the protein crystallization process to monitor and record the crystallization process. The crystal may also be observed at intermediate points during the protein crystallization process and that observation used to choose the best moment to freeze the droplet containing the crystal in the crystallization cavity structure 14.

After formation of the crystal, or, alternatively, during an intermediate point in the crystallization process, the crystal may be frozen in place without requiring transfer of the crystal from the device 10 wherein the crystal is formed. For example, after observation shows the crystal to be large enough (for example for x-ray diffraction studies at high resolution), the crystal may be frozen in place by changing the temperature of the pins using the temperature control element 200. Alternatively, the crystal or crystallizing sample may be frozen by moving the pins 11, 12 and dipping the pins 11, 12 into a cold solution, such as liquid propane or liquid nitrogen, to freeze the crystal.

Once a crystal is frozen in the pin structure, the whole device 10 and crystal complex formed therein is suitable for transport to and use in a high energy x-ray diffraction apparatus. The open pickup structures (i.e., the pins 11, 12) provides a path for x-rays to transmit into and through the crystal to the x-ray detectors.

The shape and size of the protein crystallization device 10 are specifically designed to control the rate of transpiration (i.e. evaporation), a key factor in obtaining quality crystals. According to one embodiment, the shape of the tips 11a, 12a is optimized to promote crystallization. FIGS. 7a–7h are detailed views of the tip region of the two pins 11, 12 of the two-pin fluid handling system, illustrating different shapes suitable for promoting crystallization. The sample acquisition region 14 may be spherical, cylindrical, conical, cubic or any other suitable shape. The shape and size of the cavity formed by the pins 11,12 changes the exposed surface to volume ratio of the protein drop and therefore the evaporation rate. This allows the rapid exploration of crystallization space in a short time. Finally, by controlling temperature in a controlled humidity environment, the rate of evaporation is controlled in very precise manner. This arrangement allows the evaporation rates to be controlled in a specific and flexible manner which is fine tuned by the shape and size of the crystallization cavity 14 of the device, providing fine control over the evaporation profiles. Additional refinements such as the rate of flow of dry gas can modify the water evaporation rate and therefore the protein concentration in the drop.

Figure 8:
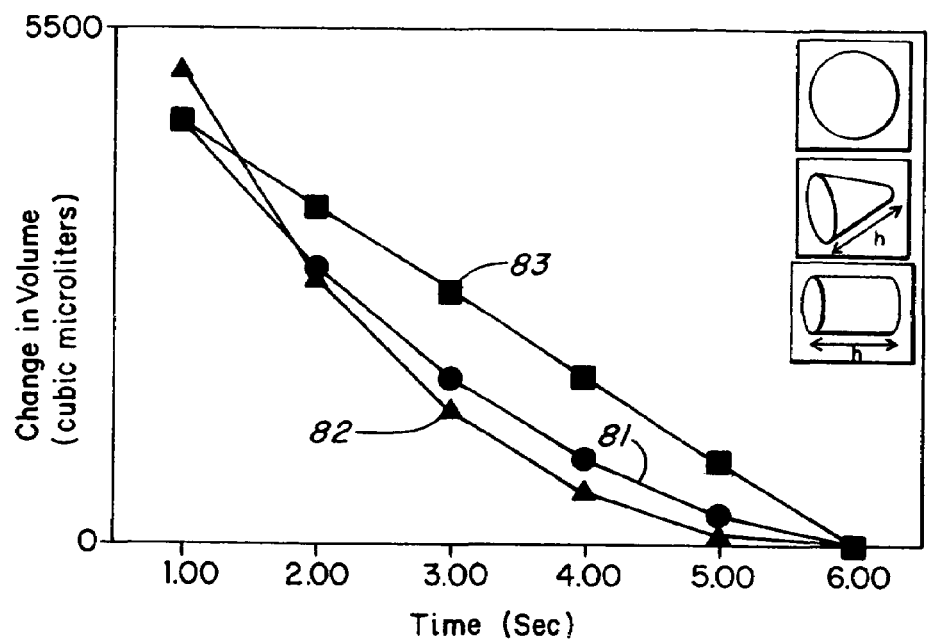
FIG. 8 is a graph showing the differences in the change in the volume for different tip shapes.

As an example of change in the rate of mass loss for different shapes, FIG. 8 shows the change in rate of volume for different shapes. The curve 81 illustrates the change in volume over time for a spherical-shaped cavity 14. The curve 82 illustrates the change in volume over time for a conical-shaped cavity 14. The curve 83 illustrates the change in volume over time for a cylindrical-shaped cavity 14.

The shape of the tips 11a, 12a may also be optimized for x-ray diffraction and for optical monitoring of the sample held between the tips.

According to another embodiment, the tips 11a, 12a may be coated in a hydrophobic, hydrophilic or other suitable material to promote the crystallization process.

Figure 7A:
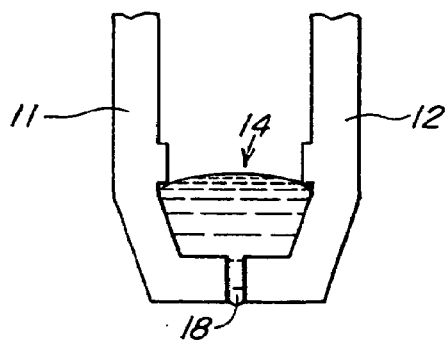
FIGS. 7a–7h are detailed views of the tip region of an exemplary pin assembly of the invention, illustrating different pin tip shapes.
Figure 7B:
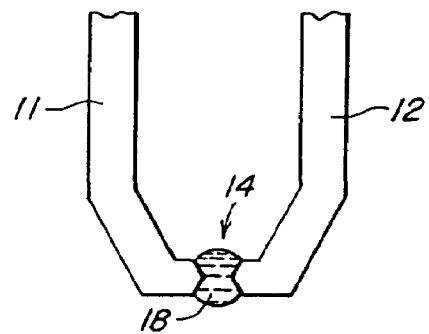
Figure 7C:
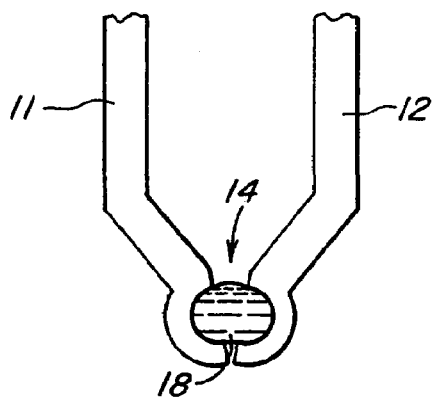
Figure 7D:
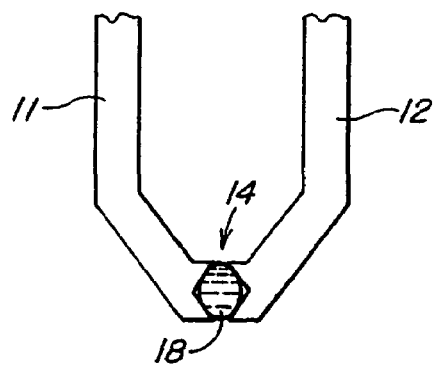
Figure 7E:
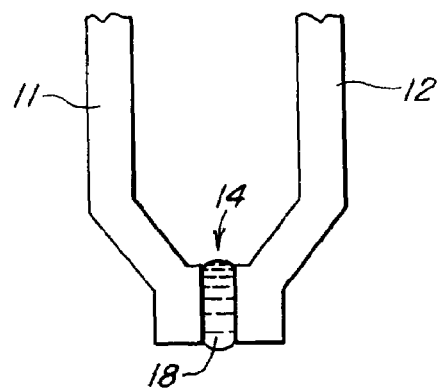
Figure 7F:
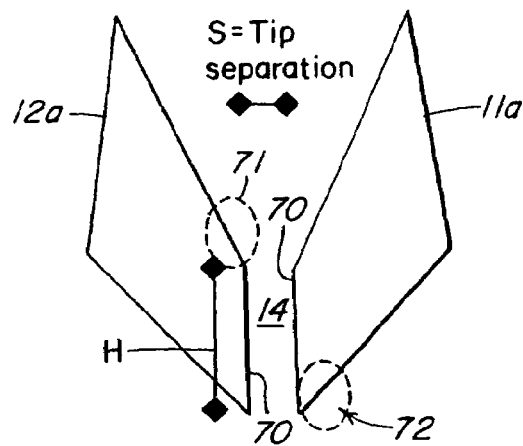
Figure 7G:
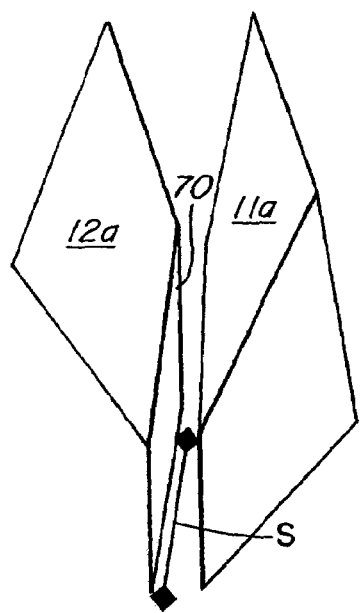
Figure 7H:
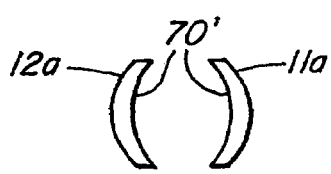

As shown in FIGS. 7f and 7g, the tip contact surfaces 70 defined by the tip heights H and tip depths S may form parallel faces or, according to another embodiment, may be tapered, so that the separation distance D is reduced towards the bottom and/or front of the tip surface. In this manner, smaller droplet volumes may be accommodated. The slope of the tips 11a, 12a may be varied in regions 71 and 72 to improve droplet shape and enhance delivery of the droplet.

FIG. 7g is a cross-sectional view of the tips 11a, 12a according to an alternate embodiment. According to the alternate embodiment, the tip surfaces 70' are curved to hold form a cylindrical or conical sample acquisition region 14 therebetween.

Figure 9:
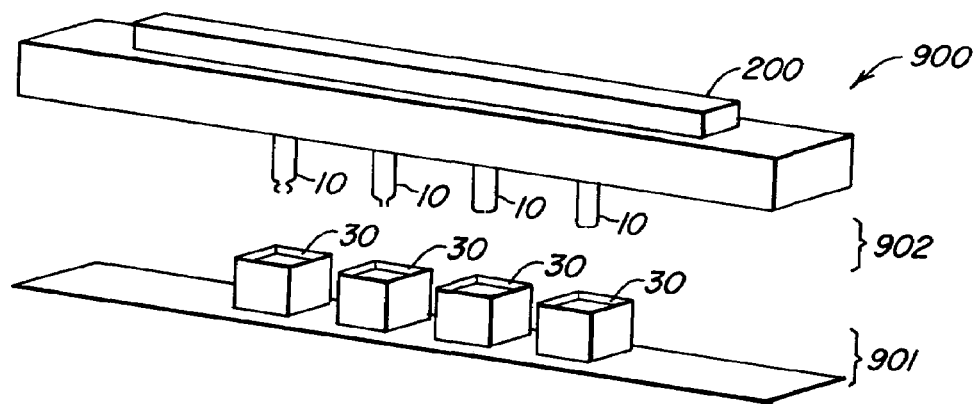
FIG. 9 is a schematic view of an array of fluid handling systems for crystallizing proteins.

As shown in FIG. 9, an array 902 of fluid handling systems or pin assemblies forming crystallization cavities for crystallizing proteins and an array 901 of wells 30 containing protein solution may be used to form a protein crystallization system 900. According to one embodiment, the array comprises an array 902 of different devices 10 comprising crystallization cavities with different sizes and shapes. Each device can be individually controlled for different temperatures in a humidity controlled environment. Such an array 900 may be used to search for desirable crystallization conditions. Different crystallization variables such as sample concentration, reagent composition and concentration, and pH can be explored. According to another embodiment, the array 902 may comprise a plurality of crystallization cavities 10 having the same size and shape under the sample temperature control. Such an array may be used for optimized conditions for crystal growth.

According to an alternate embodiment, the solution in the array of wells 901 may have varied concentrations. The concentration in the wells 30 may be varied by setting effectors, such as adding or subtracting solvents, ions, detergents, drugs, ligands, or through other suitable means. The wells may include a membrane to retain proteins while altering the concentration of the protein solution by dialysis.

The automated, flexible evaporation-controlled crystal growth system of the present invention allows for several evaporation profiles to be explored simultaneously. The invention may thus provide dynamic and real-time control of protein concentration level via control of rate of water evaporation. Smaller populations of higher quality crystals can be produced, by choosing correct evaporation profile of crystallization material.

In one embodiment, the crystals of the present invention are a family of crystals that are different space groups, e.g., geometries, symmetries, or unit cells, of the same polypeptides and nucleic acids. The present invention allows a skilled artisan to sample many more conditions, with much less protein and in a much shorter time period, than conventional techniques. These improvements make it more likely that different crystal forms of the same protein will be identified. Accordingly, the invention, at least in part, is a family of structures containing 3, 4, 5, 6, 7, 8, 9, 10, 15, 20 or 25 members that are related by the fact that they all contain the same non-solvent molecules, e.g., proteins, nucleic acids, cofactors, or substrates.

Protein crystals can be stressed and even damaged during harvesting and/or subsequent manipulations and therefore become unsuitable for data collection. The present device avoids damage by being able to grow and freeze the crystals in the crystallization cavities formed between the pin tips 11, 12.

For proteins for which solubility varies with temperature, it is advantageous to use precision temperature control as a straightforward method of controlling protein concentration.

The protein crystallization device of the present invention combines a method and device to control the evaporation of solvent from crystallization material for protein crystallization. The protein crystallization device provides significant advantages over currently used fiber loops. For example, crystals can be grown, frozen and diffraction data can be collected in the pins, without requiring extra steps for crystal handling, which typically cause considerable crystal loss.

The protein crystallization device of the present invention provides significant advantages over prior methods for crystallizing proteins and other biomolecules. The operation in microscale levels substantially reduces or eliminates convection and sedimentation due to the small size of the drop and because surface tension is the major force acting on the droplet. The crystallization device 10 is reusable, precise and provides quick, accurate and reversible temperature control. The crystallization device 10 is easier to use than prior flexible fiber loop. The crystallization device is cost effective while providing accurate and improved control of nanoliter to picoliter volumes.

The ability to optically monitor the sample acquisition region between the tips 11, 12 of the fluid handling system has additional applications in addition to protein or biomolecule crystallization. According to other embodiments, optical monitoring of a sample between the tips 11, 12 in the two-pin liquid handling system 10 may be performed for any chemical or biochemical process for which experimental measurement of optimal conditions or response to variation of conditions is desirable.

FIG. 8 illustrates another embodiment of the fluid handling system according to the teachings of the present invention. The illustrated fluid handling system 40 includes a pin assembly 40A having at least a fixed pin 41 and a movable pin 42. In the fluid handling system of FIG. 8, the resting position of a first pin 41 is fixed relative to a substrate 43 and the resting position of the second pin 42 is movable relative to the first pin 41 and the substrate 43. The fluid handling system 40 further includes a driver 44 for varying the separation distance between the tips 41a, 42a by adjusting or moving the position of the second movable pin 42 by acting upon the fulcrum region 46. According to the illustrated embodiment, the movable pin 42 rotates about a fixed pivot point 45 under the control of the driver 44 to adjust the separation distance at the tips.

The illustrated pins 41 and 42 can also include a relaxation region 51 for preventing breakage of the tips. One skilled in the art will recognize that the relaxation region 51 may be formed in one or both of the pins 41, 42 of the fluid handling system 40.

The illustrated fluid handling system 40 is formed from a silicon wafer using a standard photolithography etching process to fabricate one or more of the pin assembly including pins 41, 42, the relaxation region 51, the driver 44, and the fixed point 45 of the fulcrum region 46 in the wafer substrate 43. According to the illustrative embodiment, the fluid handling system 40 is fabricated from a silicon wafer having dimensions of about one square centimeter. The pins 41,42 have a length of about five millimeters, though one skilled in the art will recognize that the invention is not limited to this size. According to an alternate embodiment, a larger silicon wafer or other suitable substrate is provided, and an array of two-pin fluid handling systems is fabricated on the larger silicon wafer. For example, a silicon wafer having a size of about ten square centimeters may be used to fabricate an array of about seventy two-pin fluid handling systems 40 thereon. A fifteen square centimeter silicon wafer can be utilized to fabricate over one hundred two-pin fluid handling systems 40 in the silicon wafer substrate. Those of ordinary skill will readily recognize that any suitable configuration can be employed to move one or both of the pins.

Figure 10:
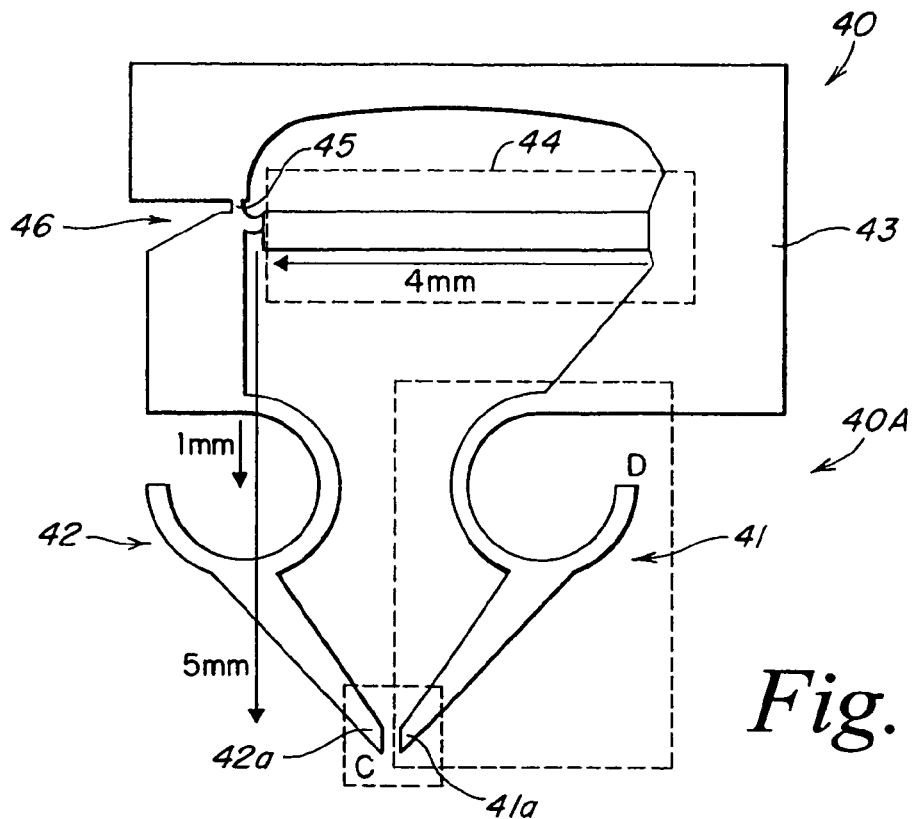
FIG. 10 is a schematic view of an alternate embodiment of the fluid handling system of the invention employing a fixed pin and a movable pin.
Figure 11:
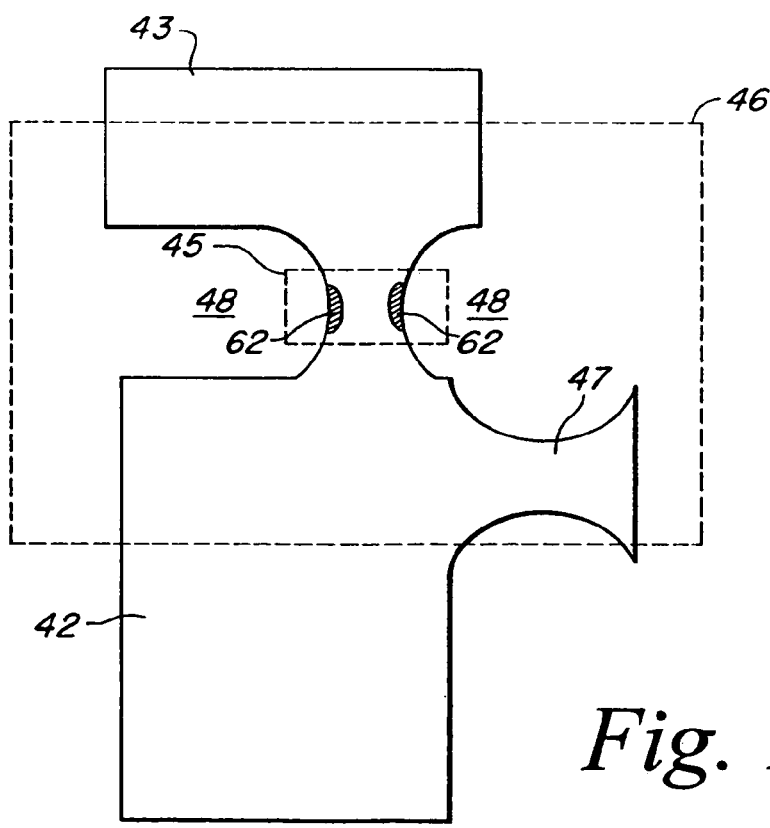
FIG. 11 is a detailed view of the fulcrum region of the fluid handling system of FIG. 8.

FIG. 11 is a detailed view of the fulcrum region 46 of the fluid handling system of FIG. 10. The movable pin 42 is configured to pivot about a fixed point 45 to vary the separation distance of the two pin tips. The driver 44 applies a force to an application region 47 of the fulcrum region 46 to cause the movable pin 42 to rotate, thereby effecting movement of the movable pin tip 42a relative to the tip 41a of the fixed pin 41. As illustrated, the fulcrum region 46 includes gaps 48 are formed in the substrate 43 adjacent to the fixed point 45 to allow for rotation of the pin 42 about the fixed point in response to activation of the driver 44.

According to an alternate embodiment of the invention, the fulcrum region can optionally include one or more bending sensors, illustrated as piezoresistors 62, on the left and right side of the fulcrum region to allow differential sensing of actual bending of the pin 42 in the fulcrum region. In this manner, the amount of bending, and the resultant tip separation distance may be controlled using a closed loop feedback system. The use of bending sensors further limits nonlinear temperature effects by allowing real-time sensing of tip displacement.

Figure 12:
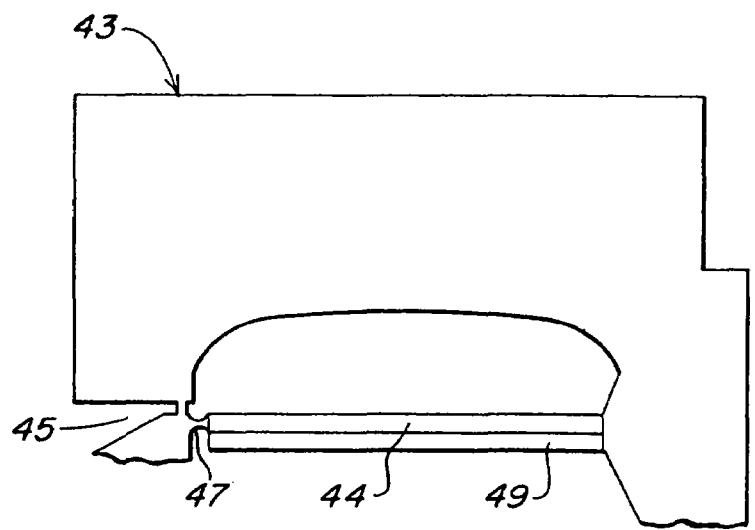
FIG. 12 is a detailed view of the driver of the fluid handling system of FIG. 10.

FIG. 12 is a detailed view of the driver 44 of the fluid handling system 40 of FIG. 10. The illustrated driver can comprise any suitable component or assembly that is capable of applying a selected force. According to one practice, the driver 44 comprise a bar of silicon that imparts a force on the application region 47 of the fulcrum 46 to move of tip 42a a predetermined amount. According to the illustrative embodiment, the driver 44 expands a predetermined amount in response to a temperature increase. The expansion of the driver 44 forces rotation of the fulcrum about the pivot point. According to the illustrative embodiment, the system is configured such that the ratio between the amount of movement of the tip 42a in response to expansion of the driver 44 to the amount of expansion of the driver is greater than one hundred. In other words, a driver expansion of one micron causes a one hundred micron displacement of the pin tip 42a.

According to the illustrative embodiment, the driver 44 has an initial length L of four millimeters. A thirty-degree rise in temperature of the silicon results in a 1.08 micrometer expansion of the driver 44. The expansion of the driver 44 forces the pin 42 to rotate about the fixed pivot point 45, thereby increasing the separation distance between the tips 41a, 42a by greater than 108 microns.

According to the illustrative embodiment, a temperature control element can be coupled or affixed to the driver 44. For example, a heating element, such as a heating resistor 49, can be optionally coupled or affixed to the driver for applying heat thereto. The heating resistors may comprise poly resistors, diffused resistors or any suitable means for applying heat to the driver 44 in order to effect controlled expansion of the driver 44 and to vary the separation distance between the tips 41a, 42a. Optionally, cooling fins (not shown) are provided in the driver 44 near the fulcrum region 45 to prevent unwanted heating of the driver in the fulcrum region. According to an alternate embodiment, a temperature sensor (not shown) in communication with the heating means is included in the fluid handling system 40 to provide closed loop control of the driver 44 temperature.

One skilled in the art will recognize that the fluid handling system is not limited to the illustrative driver. According to alternate embodiments the driver 44 comprises an electrostatic system, a piezoelectric system, an electromechanical system, a thermoelectric actuator or any suitable system for applying a predetermined and defined force to cause controlled adjustment of the separation distance between the pin tips 41a, 42a. One skilled in the art will further recognize that the fluid handling system is not limited to a fulcrum for varying the separation distance and that any suitable mechanism for varying the separation distance may be utilized.

According to alternate embodiment, the one or both of the tip surfaces 70 and/or the outside shaft surface are coated with a hydrophilic, hydrophobic or other chemical coating to enhance droplet acquisition, handling and dispensing. For example, the tips 41, 42 may be formed of or coated with a hydrophilic coating to enhance retention of a sample in the sample acquisition region. According to one embodiment, the outside shaft surfaces of the tips 41,42 are coated with gold or another suitable hydrophobic material without affecting the tip surfaces 70 defining the sample acquisition region 14. The use of a metal coating provides enhanced control over the volume and release of a droplet. The use of silicon and/or gold additionally allows for more vigorous cleaning solutions to be utilized when cleaning the tips without degrading the system. In this manner, contamination of the tips is reduced.

The coating may be applied in a pattern to the tip surfaces 70 or the other surfaces of the tips 41, 42 by shadow masking. The coating may be sputtered, or evaporated on a surface in a predetermined pattern, defined by a mask. One skilled in the art will recognize that any suitable pattern for directing the liquid sample and enhancing control over sample acquisition, handling and dispensing may be utilized.

According to another embodiment, the fluid handling system may comprise a single pin having a suitable pattern coating applied to the surfaces of the pin tip. For example, the shaft of the single pin may be coated with a suitable hydrophobic coating and the tip of the pin may be coated with a suitable hydrophilic coating to enhance acquisition, manipulation and dispensing of a liquid sample.

Figure 13:
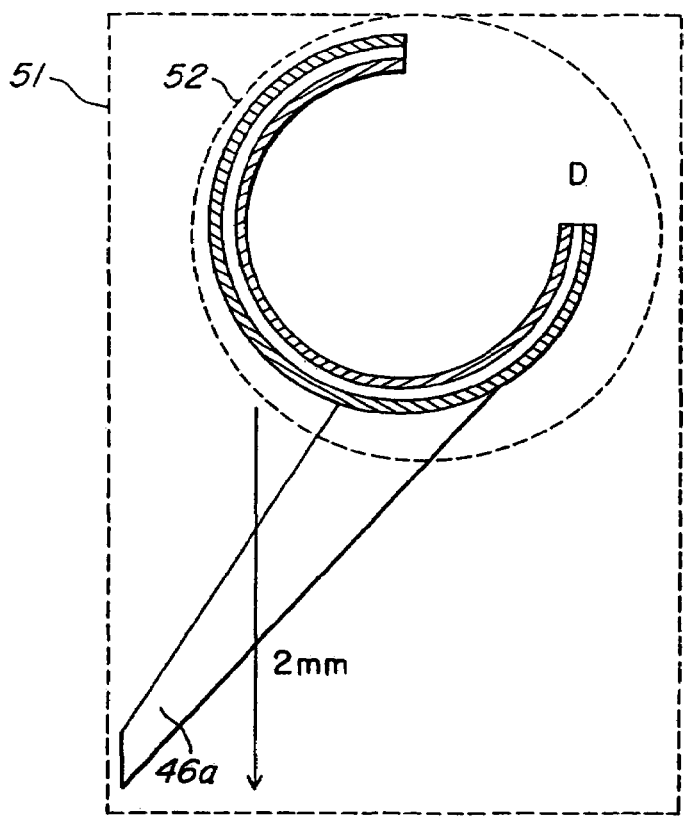
FIG. 13 illustrates the relaxation region of the fluid handling system of FIG. 10.

FIG. 13 illustrates the relaxation region 51 of the fluid handling system 40 of FIG. 8. The relaxation region can comprise any suitable part, component or feature that allows the tip to handle or absorb a force applied thereto. The pin tips 41 and 42 may be brittle and subject to breakage when accidentally touched down to surfaces, due to their size and the material used to fabricate the pins. The illustrated relaxation region 51 comprises a spring 52 formed between the tip 41a and the substrate 43. When the tip 41a contacts a surface, the spring absorbs the impulse and retracts the tip 41a to prevent breakage. The springs 52 in the pins are configured to move the corresponding tip up and away from the other tip to prevent collision of the tips. The invention is not limited to the illustrative spring design. One skilled in the art will recognize that any suitable spring design may be utilized to form the relaxation region 51 to protect the pin tips from breakage.

According to an alternate embodiment, the spring 52 includes sensors to measure of the force of contact between the tip and a surface. For example, differential piezoresistive sensors may be included in the spring 52 and connected to an actuator (not shown) to control the spring using feedback control loop. The spring sensor may also be utilized to measure the force exerted by the droplet on the tips, and allow the driver to compensate for variable forces exerted by the droplet on the tips.

According to an alternate embodiment of the present invention, a relaxation region may be implemented in a two-pin fluid handling system comprising a pair of spaced-apart, fixed pins defining a sample acquisition region of fixed volume.

As discussed, the fluid handling system 10 or 40 of the illustrative embodiment may be microfabricated from a suitable substrate, such as silicon, glass or plastic. According to the illustrative embodiment, photolithography may be utilized to form the pin structures in the substrate. In photolithography, the pattern of the two pins and other components of the two-pin fluid handling system 10 or 40 are imprinted on a silicon wafer, or other substrate, using one or more photoresist layers that are patterned by UV or other light projected through one or more photo-masks containing the pattern on it. The substrate is then etched to fabricate the two-pin structure. One skilled in the art will recognize that any suitable microfabrication technique may be utilized to manufacture the two-pin fluid handling system of the illustrative embodiment of the present invention.

One skilled in the art will recognize that the described microfabrication technique may further be utilized to fabricate single-pin fluid handling systems from a silicon wafer or other suitable substrate. For example, it is within the scope of the invention to microfabricate a single-pin structure having two tips forming a sample channel for acquiring, manipulating and dispensing a liquid sample, as described in U.S. Pat. No. 6,101,946, from a silicon wafer by etching the silicon wafer to define the pin and sample channel.

One skilled in the art will recognize that the described invention in biomolecule crystallization may be implemented with any capillary uptake structure. For example it is within the scope of the invention to pick up the biomolecule solution with a single pin with a slot or in a cavity defined by the tips of three or more pins or in a cylindrical capillary.

Figure 14:
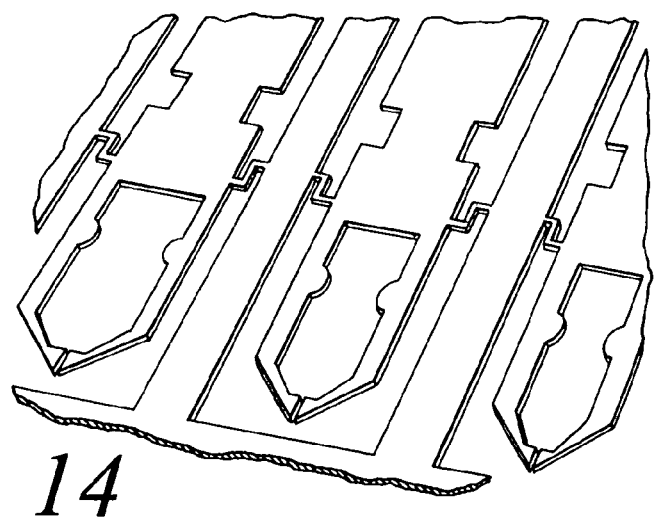
FIG. 14 is a scanning electron microscope (SEM) image of an array of two-pin fluid handling systems that are microfabricated from a silicon wafer according to the teachings of the illustrative embodiment of the present invention.

FIG. 14 is a scanning electron microscope (SEM) image of an array of two-pin sample fluid handling systems 100 according to an embodiment of the invention and formed from a silicon wafer 101 using the above-described microfabrication technique. As shown, a plurality of two-pin fluid handling systems are fabricated from a single silicon wafer substrate. Each two-pin fluid handling system comprises a pair of elongated pins that are spaced apart to define a sample acquisition region between the tips of the pins.

Figure 15:
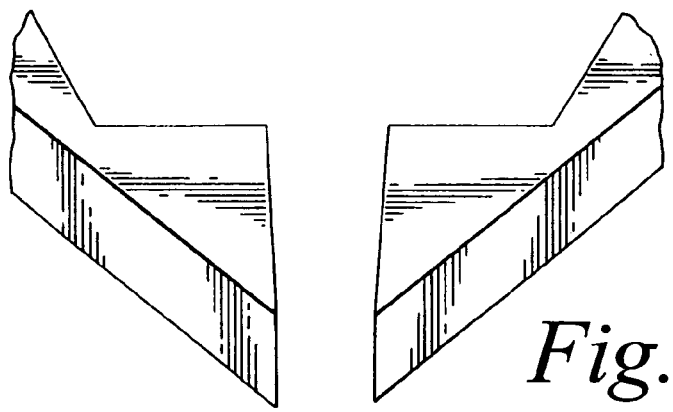
FIG. 15 is a SEM image showing a detailed view of a tip region of one of the two-pin fluid handling systems of FIG. 14.

FIG. 15 is another SEM image showing a detailed view of the tip region of one of the microfabricated two-pin fluid handling systems of FIG. 9. As shown, the pins are etched in a silicon wafer to define a sample acquisition region 140 between the tips of the pins. As illustrated, the microfabricated pin tips have a separation distance of less than about 100 microns.

Figure 16:
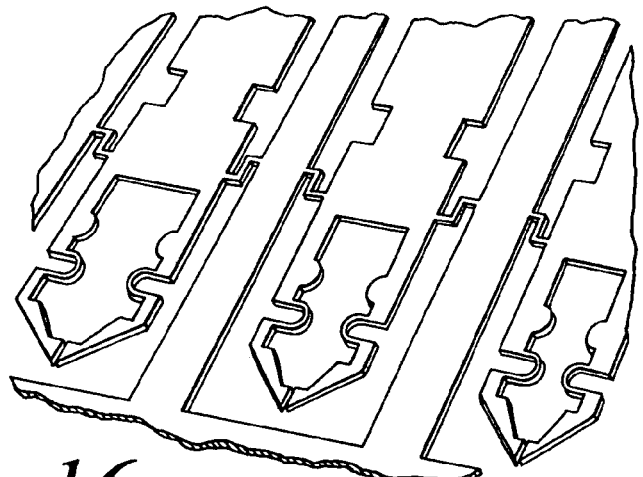
FIG. 16 is a SEM image illustrating an array of two-pin fluid handling systems having relaxation regions that are microfabricated from a silicon wafer according to the teachings of the illustrative embodiment of the present invention.

FIG. 16 is another SEM image of an array of microfabricated two-pin sample fluid handling systems 110 having relaxation regions 51 according to an embodiment of the invention. As shown, the array is also formed from a silicon wafer 101 using the above-described microfabrication technique. The relaxation region 51 is formed by etching the silicon wafer in the region between the pin tips and the holder to define a spring for absorbing an impact on the tips. The relaxation region 51 prevents breakage of the pin tips 41, 42 when the pin tips contact a surface.

The fluid handling system provides significant improvements to the process of forming, manipulating and dispensing droplets of samples for spotting and dilution applications. The illustrative configuration provides precise control over the amount of liquid sample that is acquired and deposited through the use of two pins having a variable separation distance. Adjusting the separation distance between the pin tips easily and precisely modifies the volume of the acquired liquid droplet and the deposited liquid droplet. Furthermore, measurements of the physical properties of the liquid volume can be made on the fly and the tip separation can be modified quickly and easily to compensate for variations. The use of sensors provides precise control of the tip separation distance to optimize the process of acquiring, manipulating and dispensing droplets of a liquid sample.

The present invention has been described relative to an illustrative embodiment. Since certain changes may be made in the above constructions without departing from the scope of the invention, it is intended that all matter contained in the above description or shown in the accompanying drawings be interpreted as illustrative and not in a limiting sense.

It is also to be understood that the following claims are to cover all generic and specific features of the invention described herein, and all statements of the scope of the invention which, as a matter of language, might be said to fall therebetween.

Having described the invention, what is claimed as new and protected by Letters Patent is:

The invention claim is:

1. A method for crystallizing biomolecules, comprising the steps of:
providing a liquid handling assembly comprising a plurality of components formed on a single substrate for handling a fluid, the plurality of components comprising a holder, a first pin extending from and integral with the holder, a second pin extending from and integral with the holder, the second pin spaced from the first pin to define a channel therebetween sized and dimensioned for receiving and retaining a fluid sample by capillary action;
acquiring a droplet of a biomolecule solution in the channel;
transpiring water between the biomolecule solution and the environment to concentrate the biomolecule, thereby causing crystallization of the biomolecule to occur within the channel.

2. The method of claim 1, wherein the channel has a capacity of between about 0.1 nanoliters and about 50 nanometers.

3. The method of claim 1, further comprising the step of:
observing formation of a crystal.

4. The method of claim 3, wherein the step of observing comprises detecting biomolecule aggregation by laser scattering.

5. The method of claim 3, wherein the step of observing comprises using an optical device selected from the group consisting of a polarization microscope, a CCD camera, and a video camera.

6. The method of claim 1, further comprising the step of freezing the crystal on the pin.

7. The method of claim 1, wherein the step of acquiring a droplet of biomolecule solution comprises dipping the pin in a well containing a supply of the biomolecule solution and a crystallization reagent.

8. The method of claim 1, wherein the step of transpiring comprises controlling the temperature of one of the first pin and the second pin.

9. The method of claim 1, wherein the first pin and second pin are separated by a distance of less than about 100 microns where the channel is formed.

10. The method of claim 1, wherein the first pin has a first tip having a concavely curved surface and the second pin has a second tip with a concavely curved surface spaced a predetermined separation distance from the first tip to define the channel between the concavely curved surfaces.

11. The method of claim 10, wherein the concave surface of the first tip faces and the predetermined separation distance between the two concave surfaces is less than about 100 microns.

12. The method of claim 1, wherein each pin has a tip defining a side of the channel, and each tip comprises a body connecting the tips to the holder, and the body of the first pin is separated from the body of the second tip by a second distance that is larger than the predetermined separation distance between the first tip and second tip.

13. The method of claim 8, wherein the step of controlling the temperature employs a Peltier element.

14. The method of claim 3, further comprising the step of altering crystallization conditions in response to the step of observing.

15. The method of claim 14, wherein the step of altering comprising varying the temperature of the crystallizing structure.

16. The method of claim 14, further comprising the steps of:
   recording the crystallization conditions; and
   observing the crystal formed in the channel.

17. The method of claim 8, wherein the liquid handling system further comprises a temperature control element, a temperature sensor for sensing the temperature of the system, and a controller in circuit with the temperature control element and the temperature sensor for controlling the temperature of the liquid handling system.

18. The method of claim 8, wherein the substrate comprises a silicon wafer.

* * * * *